United States Patent [19]
Van Leengoed et al.

[11] Patent Number: 5,254,340
[45] Date of Patent: Oct. 19, 1993

[54] **VACCINE SUITABLE FOR PROPHYLAXIS AND CONTROL, RESPECTIVELY, OF THE PIG DISEASE CAUSED BY *HAEMOPHILUS PLEUROPNEUMONIAE* AND A METHOD FOR OBTAINING EXTRACELLULAR PROTEINACEOUS MATERIAL OF *HAEMOPHILUS PLEUROPNEUMONIAE* FOR USE IN SUCH VACCINES**

[75] Inventors: Leonardus A. M. G. Van Leengoed; Elbarte M. Kamp, both of Lelystad, Netherlands

[73] Assignee: Centraal Diergeneeskundig Instituut, Lelystad, Netherlands

[21] Appl. No.: 392,781

[22] Filed: Aug. 11, 1989

[30] Foreign Application Priority Data

Aug. 12, 1988 [NL] Netherlands ............... 8802007

[51] Int. Cl.⁵ .............. A61K 39/02; A61K 39/00
[52] U.S. Cl. ........................ 424/92; 424/88
[58] Field of Search ............. 424/88, 92; 530/300

[56] References Cited

FOREIGN PATENT DOCUMENTS

80/02113 11/1980 PCT Int'l Appl. .

OTHER PUBLICATIONS

Frey et al. FEMS Microbiology Letters 55:41-46 1988.
Maudsley et al., Canadian Journal of Microbiology 32:801-805, 1986.
Rosendal et al., Am J Vet Res-vol. 49 Jul. 1988, Evaluation of heat-sensitive, neutrophil-toxic, and hemolytic activity of *Haemophilus* (Actinobacillus) *pleuropneumoniae* pp. 1053-1058.
Lenser et al. (abstract) Vet Microbiology pp. 335-338. Protection of mice against the lethal effect of an intraperitoneal infection with *H.* (Actinobacillus) *pleuropneumoniae*.
Nielsen et al. (abstract) Nordisk Veterinaermedicin 1984 pp. 221-234 vol. 36. *Haemophilus pleuropneumoniae* serotypes-cross protection experiments.
Bloxham (abstract) Irish Veterinary news 1987 vol. 9 pp. 37-38 Preliminary results on the efficacy of a *H. pleuropneumoniae* vaccine in pigs.
American Society for Microbiology, vol. 87, No. 0, 1987, p. 40, summary No. B-91, U.S.; P. J. Fedorka-Cray et al.
Abstracts of the Annual Meeting of the American Society for Microbiology, (88th Annual Meeting, 8-13 May 1988, Miami Beach, Fla.), vol. 88, No. 0, p. 35, summary No. B-37, P. J. Fedorka-Cray et al.

*Primary Examiner*—Christine M. Nucker
*Assistant Examiner*—H. Sidberry
*Attorney, Agent, or Firm*—Bachman & La Pointe

[57] ABSTRACT

The invention relates to a vaccine suitable for the prophylaxis and control respectively of *Haemophilus pleuropneumoniae*, advantageously of all the serotypes of *H. pleuropneumoniae*, which vaccine is based on an effective content of a mixture of extracellular proteinaceous material derived from the culture medium of strains of at least two different serotypes of *H. pleuropneumoniae* preferably derived from the culture medium of at least one *H. pleuropneumoniae* strain selected from the group of serotypes 1,5,6,9 and 11 on the one hand and from the culture medium of at least one *H. pleuropneumoniae* strain selected from the group of serotypes 2, 3, 4 and 8 on the other hand.

2 Claims, 3 Drawing Sheets

VACCINE SUITABLE FOR PROPHYLAXIS AND CONTROL, RESPECTIVELY, OF THE PIG DISEASE CAUSED BY *HAEMOPHILUS PLEUROPNEUMONIAE* AND A METHOD FOR OBTAINING EXTRACELLULAR PROTEINACEOUS MATERIAL OF *HAEMOPHILUS PLEUROPNEUMONIAE* FOR USE IN SUCH VACCINES

BACKGROUND OF THE INVENTION

The invention relates to vaccines suitable for the prophylaxis and control, respectively, of the pig disease caused by *Haemophilus pleuropneumoniae* as well as to a method for obtaining an extracellular proteinaceous material of *Haemophilus pleuropneumoniae*, suitable for use in such vaccines.

*H. pleuropneumoniae* is the causative agent of *Haemophilus pleuropneumonia* in pigs which at present is regarded as being one of the most important disorders of the bronchial tubes in these animals (see, inter alia, Maudsley J. R. et al. Can. J. Microbiol. 32, (1986), pages 801–805). The principal symptoms in the acute stage of this disease are the occurrence of high fever and an extensive fibrinous hemorrhagic necrotic lobar pneumonia, which is accompanied by fibrinous pleurisy. It is assumed that one or more toxins produced by *H. pleuropneumoniae* play a significant role in the above pathogenisis. More particularly, it has been observed that endobronchial administration of both sonificated non-viable *H. pleuropneumoniae* cells and a cell-free supernatant obtained from a culture medium for *H. pleuropneumoniae* to pigs results in local pneumonia which corresponds to the pneumonia which occurs in experimentally infected pigs. The article by Maudsley J. R. et al, (Can. J. Microbiol. 32, 801–805 (1986)) particularly concentrates on obtaining a hemolysin product produced by *H. pleuropneumoniae* with the aid of a chemically defined medium (CDM) which does not contain proteins, so that the extracellular hemolysin product obtained with the aid of *H. pleuropneumoniae* strain 12864 (serotype 3) can be separated off in a relatively simple manner; the product found according to Maudsley et al. appears in experiments to be a heat-labile protein which for the time being, however, cannot be used for vaccination purposes. The said hemolysin product induces hemorrhagic pneumonia in mice.

In "Abstracts of the Annual Meeting of the American Society for Microbiology", Vol. 87, No. 0, 1987, page 40, Summary No. B-91, P. J. Fedorka et al, it is indicated that a hemolytic factor and a cytotoxic factor from *H. pleuropneumoniae* serotypes 1 and 5 were identified, which factors were heat-labile and pH sensitive. After administration thereof to either pig lung macrophages or mice said factors apparently showed the relevant activity. At the end of this summary it is brought up that isolation of these virulence factors may aid in vaccine development and disease irradiation. However, nothing is mentioned or even suggested therein concerning a universal vaccine which may cope with the majority or even all the serotypes of *H. pleuropneumoniae*.

Further in "Abstracts of the Annual Meeting of the American Society for Microbiology", Vol. 88, May 8-13, 1988, No. 0, page 35, Summary B-37, P. J. Fedorka et al, it is mentioned that a dialysed hemolysin derived from *H. pleuropneumoniae* serotype 1 was suitable as the active component of a vaccine. Such a vaccine would provide a marked protection from clinical disease and lung pathology after a challenge with the serotype strain in question. At the end of this summary it is stated that apparently the hemolysin is the major immunogen for protection in the *H. pleuropneumoniae* induced disease. In this respect, however, it is emphasized that in this last reference nothing is mentioned about the cytotoxic factor of the microorganism in question or the development of a universal vaccine against the many different serotypes of *H. pleuropneumoniae*.

SUMMARY OF THE INVENTION

In view of the need for an adequate therapy for *H. pleuropneumonia* in pigs, since this disease caused by bacterial infection has an endemic course and a high death rate, applicant has made an extensive research concerning the development of a vaccine which should be suitable for the prophylaxis and control, respectively, of the majority of the known serotypes of *H. pleuropneumoniae* and advantageously all serotypes of *H. pleuropneumoniae*. In this respect it is remarked that at present twelve serotypes of *H. pleuropneumoniae* are known, while the occurrence of these serotypes may differ between regions.

Surprisingly it has been found that the above object can be achieved by means of a vaccine which is characterized by an effective content of a mixture of extracellular proteinaceous material derived from the culture medium of strains of at least two different serotypes of *H. pleuropneumoniae*.

In particular the invention relates to a vaccine which comprises an effective content of a mixture of extracellular proteinaceous material derived from the culture medium of at least a *H. pleuropneumoniae* strain selected from the group of serotypes 1,5,6,9 and 11 on the one hand and extracellular proteinaceous material derived from the culture medium of at least a *H. pleuropneumoniae* strain selected from the group of serotypes 2,3,4 and 8 on the other hand.

DETAILED DESCRIPTION OF THE PREFERRED EMBODIMENTS

Figure 1:
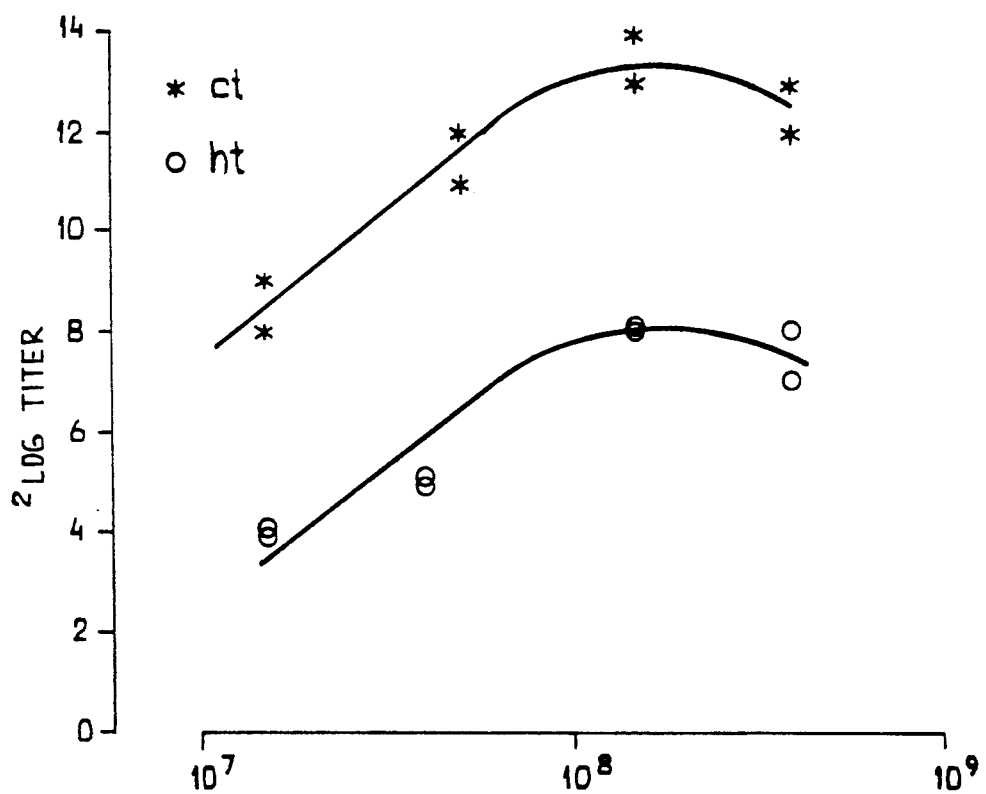
FIG. 1 is a graphic representation of the CT and HT production with an inoculation with a bacteria suspension of the *H. pleuropneumoniae* strain 13261 of $10^7$–$10^9$ CFU/ml.

The extracellular proteinaceous materials in question can be obtained by a) culturing a *H. pleuropneumoniae* strain on a culture medium to which nicotinamide adenine dinucleotide (NAD) has been added;

b) transferring the organisms of *H. pleuropneumoniae* obtained in (a) to a culture medium which is enriched with serum or serum products and does not contain NAD; and c) sterile filtration of this medium to give a filtrate.

The filtrate obtained in the above manner may be processed further, where necessary, by 1) concentrating the filtrate in question, for instance by mixing it with a salt containing solution like an ammonium sulphate solution (advantageously a solution saturated to more than 50 per cent) to give a precipitate;

2) dissolving the precipitate obtained in (1) in a phosphate-buffered physiological saline solution (PBS); and 3) dialysing the product obtained in (2) against PBS to give a dialysed proteinaceous material.

The filtrate, or proteinaceous material, obtained in the above manner has been found to be capable of generating antibodies in pigs. As a result thereof pigs vaccinated with a mixture of proteinaceous materials defined according to the invention surprisingly become immune to infection by *H. pleuropneumoniae*.

More particularly, *H. pleuropneumoniae* is cultured in the above step (a) on, for example, sheep's blood agar to which 0.1% nicotinamide adenine dinucleotide (NAD, Flucka) has been added. The blood agar plates are washed after an incubation of, for example, 6-8 hours at approximately 37° C. and ±5-10% $CO_2$. The organisms thus obtained are used, in accordance with above step (b), to inoculate a fluid medium containing serum or serum products and not containing NAD. The whole is incubated at a temperature of about 37° C. The inoculated medium is then sterilised by means of, for example, filtration.

Commercially available filters may be used for carrying out the filtration in step (c) according to the invention. Examples thereof are the Millex GV membrane filters having a pore size of 0.2 μm and then Gelman Mini Capsule filter having a pore size of 0.45 μm (Gelman Sciences Inc.).

The filtrate obtained may be processed further, where necessary, by dropwise addition of 1 part by volume of a saturated salt solution, for instance an ammonium sulphate solution to 1 part by volume of filtrate. The precipitate is then collected by means of centrifuging. The precipitate obtained is then dissolved in PBS and dialysed against PBS. The dialysed material can then be used for preparation of the vaccine. Furthermore, this dialysed material may be used for characterizing specific toxins present therein, such as the cytotoxic toxin (CT) and the hemolysing toxin (HT).

The course of the production of the above toxins CT and, if present, HT can be determined or monitored by incubating samples of the inoculated medium of step (b) with lung macrophages or with erythrocytes. For example, lung macrophages of pigs and erythrocytes of sheep may be used for this purpose. The dilution of the sample which still just results in cell death of the macrophages or lysis of the red blood cells is a measure for the toxin concentration in the medium. The biological activity of CT and of HT is understood to mean, respectively, the cell death caused by CT and the lysis of the erythrocytes caused by HT.

The product obtained in the above manner can be characterized as follows:

1) Biological properties: the product dialysed against PBS has cytotoxic activity and, depending on the cultured serotype, hemolysing activity. Moreover, the dialysed product, when administered endobronchially to pigs, causes a pleuropneumonia which is histologically identical to the pleuropneumonia caused by *H. pleuropneumoniae* organisms.

2) Temperature: freezing the dialysed product at −20° C. or −70° C. for 48 hours has no influence on the CT activity and on the HT activity which may be present. After heating the product at 120° C. for 1 hour, the biological activity of CT in lung macrophages of pigs and the possibly present activity of HT in erythrocytes of sheep are no longer detectable.

3) pH: pH changes with NaOH and HCl for 2 hours at room temperature do not lead to inactivation of CT and the possibly present HT of the dialysed product.

4) Proteolytic enzymes: incubation of the dialysed product at 37° C. for 1 hour with Dyspase II, a protease, inactivates the CT and the possibly present HT activity.

5) Shelf life: the CT and possibly present HT activities of undialysed and dialysed product remain at −20° C. for several months.

6) Molecular weight of CT and HT: The native CT/HT of serotypes 2 and 9 have a molecular weight, which is somewhat higher than 200 kD or 400 kD respectively with a Superose 6 column or Superose 12 column; this difference is probably caused by complex formation. In an SDS-page the purified CT/HT of serotype 9 consists of two bands, both having a molecular weight of 100±10 kD. The CT/HT does not pass through a Pm 30,000 amicon filter.

7) Protection: pigs vaccinated with the dialysed product develop antibodies which neutralise the activity of CT and of HT. Pigs with these neutralising antibodies do not develop acute pleuropneumonia after infection with an *H, pleuropneumoniae* culture.

As mentioned above twelve serotypes of *H. pleuropneumoniae* are known to date. Investigation of field strains of *H. pleuropneumoniae* has shown that the differences in toxin production (CT and possibly HT) are dependent on the serotype and not dependent on the strain.

Table A, as indicated below shows the results of the cross neutralization of hemolysin produced by serotype reference strains of *H. pleuropneumoniae* by antisera raised against cytoxin/hemolysin preparations of the strains in question. Table B which follows shows the CT production of eleven serotypes of *H. pleuropneumoniae*, and the neutralisation titers with the aid of an antiserum, generated in rabbits with the aid of the product dialysed in the above manner.

TABLE A

Cross neutralization of hemolysin produced by serotype reference strains of *H.pleuropneumoniae* by antisera raised against cytotoxin/hemolysin preparations of these strains.

| Hemolysin of strain | sero type | antiserum against cytotoxin/hemolysin preparations of serotype | | | | | | | | | | |
|---|---|---|---|---|---|---|---|---|---|---|---|---|
| | | 1 | 2 | 3 | 4 | 5 | 6 | 7 | 8 | 9 | 10 | 11 |
| S4047 | 1 | 64[a] | − | − | − | + | + | − | − | + | + | + |
| K17 | 5 | + | − | − | − | 128 | + | − | − | + | + | + |

TABLE A-continued

Cross neutralization of hemolysin produced by serotype reference strains of *H.pleuropneumoniae* by antisera raised against cytotoxin/hemolysin preparations of these strains.

| Hemolysin of strain | sero type | antiserum against cytotoxin/hemolysin preparations of serotype ||||||||||| 
|---|---|---|---|---|---|---|---|---|---|---|---|---|
| | | 1 | 2 | 3 | 4 | 5 | 6 | 7 | 8 | 9 | 10 | 11 |
| 13261 | 9 | + | − | − | − | + | + | − | − | 128 | + | + |
| D13039 | 10 | + | − | − | − | + | + | − | − | + | 256 | + |
| 56153 | 11 | + | − | − | − | + | + | − | − | + | + | 512 |

[a]:Homologous neutralization titers are expressed as the reciprocal of the highest dilution showing less than 50% hemolysis.
+: Heterologous titer differs less than 4 times from the homologous titer.
−: No neutralization.

TABLE B

Cross neutralization of cytotoxin produced by serotype reference strains of *H.pleuropneumoniae* by antisera raised against cytotoxin/hemolysin preparations of these strains.

| cytotoxin of strain | sero type | antiserum against cytotoxin/hemolysin preparations of serotype ||||||||||| 
|---|---|---|---|---|---|---|---|---|---|---|---|---|
| | | 1 | 2 | 3 | 4 | 5 | 6 | 7 | 8 | 9 | 10 | 11 |
| S4074 | 1 | 64[a] | − | − | − | + | + | − | − | + | − | + |
| K17 | 5 | + | − | − | − | 256 | + | − | − | + | − | + |
| 13261 | 9 | + | − | − | − | + | + | − | − | 512 | − | + |
| S6153 | 11 | + | − | − | − | + | + | − | − | + | − | 512 |
| 1536 | 2 | − | 256 | + | + | − | − | − | + | − | − | − |
| 1421 | 3 | − | + | 256 | + | − | − | − | + | − | − | − |
| M62 | 4 | − | + | + | 64 | − | − | − | + | − | − | − |
| 405 | 8 | − | + | + | + | − | − | − | 512 | − | − | − |
| WF83 | 7 | ± | ± | − | ± | ± | ± | 32 | − | ± | − | ± |
| 8329[b] | 12 | + | + | − | + | + | + | + | − | + | − | + |
| D13039 | 10 | + | − | − | − | + | + | − | − | + | 512 | + |

[a]: Homologous neutralization titers are expressed as the reciprocal of the highest dilution showing less than 50% viable macro-phages.
+: Heterologous titer differs less than 4 × from the homologous titer.
−: No neutralization.
±: Heterologous titer differs more than 4 × from the homologous titer.
[b]: Serotype 12 was not available at the time of antiserum preparation and during most of this study. Therefore no homologous titer is given and no discrimination is made between − or ±.

A cross-neutralization between serotypes 1, 5, 9, and 11 clearly appears to occur from the above Tables A and B respectively. *Serotype 6, which does not itself form CT, does produce an antiserum with antibodies which belong to the strains of the said serotypes 1, 5, 9, and 11. The group with serotypes 2, 3, 4 and 8 is mentioned as a second group of mutually related serotypes.

Finally, the strain of serotypes 7 and 12 occupy a separate position. Strains of these serotypes are in fact neutralised by antisera from the two above-indicated groups, namely 1, 2, 4, 5, 6, 9 and 11, but not with the sera of serotypes 3, 8 and 10. Furthermore, the antiserum derived from the strain of serotype 7 neutralises strains of the serotypes 7 and 12 respectively.

In summary, it can be deduced from the above Tables A and B that vaccines built up from the two above-mentioned groups. Namely, on the one hand, of serotypes 1, 5, 6, 9, and 11 and, on the other hand, of serotypes 2, 3, 4 and 8, bring about a neutralisation effect which is useful for all serotypes. The invention therefore particularly relates to vaccines which are based on a combination of the extracellular proteinaceous material, obtained in the above way, of *H.pleuropneumoniae* strains, of which at least one strain belongs to the first-mentioned group of serotypes 1, 5, 6, 9, and 11, for example serotype 9, and the other strain belongs to the last-mentioned group of serotypes 2, 3, 4 and 8, for example serotype 8.

Therefore, it follows from the above that it is possible with the aid of the above-indicated combination to develop a vaccine which possesses an action against all serotypes investigated to date, namely serotypes 1-12, so that the invention provides a vaccine which is virtually universally applicable.

The methods and materials known from the state of the art in this field are suitable for carrying out the preparation method according to the invention. More particularly, a "chemically defined medium" (CDM), the composition of which is reported in the above-mentioned literature reference Can. J. Microbiol. vol. 32, (1986), page 802, may be used as growth medium in step (a) of the above-reported method according to the invention. Other growth media are trypticase-soya bean agar with 0.6% yeast extract (TSBYE) and heart infusion agar (Difco) supplemented with 5% defibrinated sheep's blood (HIS).

Furthermore, the strains known from the literature, such as ATCC 27088 (serotype 1), can be used in the method according to the invention. The *H.pleuropneumoniae* strains used in the present investigation were either traced by the applicant or were obtained from Research Institutes working in this field. More particularly, strains Shope 4074, 1536, 1421 (ATCC 27090), M62 (ATCC 33378) and K17 (ATCC 33377), which are reference strains for serotypes 1-5, were obtained from J. Nicolet (University of Bern, Switzerland), strain Femφ, which is the reference strain for serotype 6, was obtained from R. Nielsen, State Veterinary Serum Laboratory, Copenhagen, Denmark (ATCC 33590), strain WF83, which is the reference strain for serotype 7, was obtained from S. Rosendal (Dept. Vet. Microbiol., University of Guelph, Guelph, Ontario), strains 405, D13039 and 8329, which are the reference strains for serotypes 8, 10 and 12, were obtained from R. Nielsen (State Veterinary Serum Laboratory, Copenhagen, Denmark) and strains 13261 and 56153, which are the reference strains for serotypes 9 and 11, were obtained from the applicant herself. Classification of the strains into the particular serotypes is generally known from the state of the art. An indication thereof is given in Veterinary Microbiology 13 (1987), pages 249-257.

The invention is illustrated in more detail with reference to the examples below.

EXAMPLE I

Step (a)

Preparation of the inocula

The H.pleuropneumoniae strain 13261 was cultured on sheep's blood agar supplemented with 0.1% nicotinamide adenine dinucleotide (NAD) (SBV). The SBV plates were incubated at 5% $CO_2$ and at 37° C. for 6 hours. Thereafter, the plates were rinsed with 5 ml Eagle's Minimum Essential Medium (EMEM) with Earle's salts and the resultant bacterial suspension was stored overnight at 4° C., after which this was used the next day. The number of colony-forming units (CFU) was determined by inoculating ten-fold dilutions of the bacterial suspension on SBV.

Step (b)

The production step for the cytotoxin and hemolysin (HT) was carried out as follows.

Twelve media, as shown in Table C, were inoculated with $2 \times 10^8$ CFU H.pleuropneumoniae 13261 per ml. The cultures were incubated at 37° C. in a shaking incubator for 6 hours.

Step (c)

Sterile filtration of the bacterial medium

After centrifuging (10 minutes at $800 \times g$) of the bacterial suspensions the supernatants were sterilised with the aid of a filter (0.2 μm; Gelman), after which the CT and HT titers were determined. The CT titer was expressed as the reciprocal value of the maximum dilution of the supernatant which coloured all the alveolar macrophage dilutions with nigrosin, and the HT titer was expressed as the reciprocal value of the maximum dilution which hemolysed 50% SRBC (sheep red blood cells).

TABLE C

| Media | CT titer | HT titer |
| --- | --- | --- |
| EMEM (Eagle's Minimum Essential Medium) | 256 | 4 |
| EMEM + 10% Serum Plus (KC Biologicals) | 8192 | 256 |
| EMEM + 10% Serum Plus + 0.1% NAD | 1024 | 32 |
| EMEM + 10% SPF Swine serum (SWS) | 8192 | 128 |
| EMEM + 0.1% glucose | 8 | 0 |
| EMEM + 1% BSA (Sigma) | 8 | 2 |
| EMEM + 1% hydrolysed BSA | 8 | 2 |
| EMEM + 10% KC2000 (KC Biologicals) | 8 | 2 |
| EMEM + 0.5% transferrin (Sigma) | 32 | 4 |
| PBS* | 0 | 0 |
| PBS + 10% Serum Plus (KC Biologicals) | 32 | 4 |

*PBS: 0.123 M NaCl + 0.01 M $Na_2HPO_4$ + 0.0032 M $KH_2PO_4$; pH = 7.2

The $2 \times 10^8$ CFU/ml H.pleuropneumoniae 13261 used in the CT and HT production step (step b) is connected with the optimum, illustrated in FIG. 1, for the CT and HT production. As evident in this Figure, an inoculation with a bacterial suspension of more than $10^9$ CFU/ml does not result in a higher toxin production.

As can be derived from the above Table C, the culture media enriched with serum or serum products and not containing NAD give by far the highest CT and HT titers; these titers have a value such that effective vaccines against Haemophilus pleuropneumoniae can be prepared from the supernatants obtained, optionally after further processing such as concentration.

The above method according to the invention was repeated with the other strains of serotypes 1-12 given in Tables A and B. These tests showed, however, that all the strains cultured by the method according to the invention (except for strain Femφ of serotype 6) produce the cytotoxin, while the hemolysin production could be observed only in the case of strains of serotypes 1, 5, 9, 10 and 11.

EXAMPLE II

This example shows the immunity of SPF pigs vaccinated with the vaccine according to the invention against H. pleuropneumoniae.

Step (a)

Preparation of the inocula

The H. pleuropneumoniae strain 13261 was cultured on sheep's blood supplemented with 0.1% nicotinamide adepine dinucleotide (NAD) (SBV). The SBV plates were incubated at 5% $CO_2$ and at 37° C. for 6 hours. Thereafter, each plate was rinsed with 5 ml Eagle's Minimum Essential Medium with Earle's salts (EMEM). The resulting bacterial suspension was stored at 4° C. overnight, after which it was used the next day.

Step (b)

The toxin production step

Serum Plus (Hazleton Research Products Inc., Lenexa, Kans., USA) was dialysed against EMEM (v/v 9:1) while stirring continuously for 24 hours. 2.5% Serum Plus was added to the conditioned EMEM and inoculation was carried out with $2.10^8$ CFU/ml of the bacterial suspension prepared according to Step (a). The culture was incubated at 37° C. for 6 hours. The culture was then centrifuged (15 min. $\times$ 4000 g), after which an equal volume of a saturated ammonium sulphate solution was slowly added to the supernatant. The supernatant was stored overnight at 4° C. while stirring continuously and centrifuged the next day (60 min $\times$ 8000 g). The precipitate was dissolved in a phosphate-buffered salt solution (PBS; 0.123M NaCl, 0.01M $Na_2HPO_4$, 0.0032M $KH_2PO_4$; pH 7.2) and dialysed against PBS for 24 hours, filtered (Gelman 0.2 μm) to give a sterile product and finally emulsified in oil (v/v 1:1).

Step (c)

Vaccination of pigs

Specific pathogen-free (SPF) pigs (cross-bred Great Yorkshire $\times$ Dutch Landrace) 6 weeks of age were used for the vaccination test. In this test, 6 pigs were vaccinated intramuscularly at six and ten weeks, while four pigs were used as control animals. Four days before infection, in the twelfth week, the pigs were catheterised in the ear vein to make frequent blood sampling possible. The blood samples were collected from the ear vein catheter in evacuated EDTA, Li heparine and serum tubes. Samples were taken from the pigs before vaccination and twice a day during the four days preceding the inoculation and at the post-inoculation hours (PIH) 0, 2, 4, 6, 9, 12, 18, 24, 30, 36, 42 and 48. The body temperature of the pigs was determined when the blood samples were taken and the pigs were inspected for clinical signs. 48 hours after the inoculation, the pigs were killed by intravenous injection of a barbiturate and immediately subjected to necropsy.

Infection took place by means of an endobronchial inoculation. Here, the pigs were stunned with diazepam (Hoffman La Roche) and brought with their heads in a vertical position. A catheter (Cordis Europa N.V., Netherlands) was subsequently introduced through the larynx deep into the bronchi, after which 10 ml of the inoculation liquid, which contained $10^3$ CFU of $H.$ $pleuropneumoniae$ strain 13261, was slowly injected. The catheter was then quickly removed and the throats of the pigs were massaged to prevent coughing.

RESULT

After endobronchial inoculation of $10^3$ CFU $H.$ $pleuropneumoniae$ strain 13261, all non-vaccinated pigs were affected and showed difficult breathing from PIH 9 onwards, while the vaccinated pigs showed no sign of clinical disease.

Figure 2:
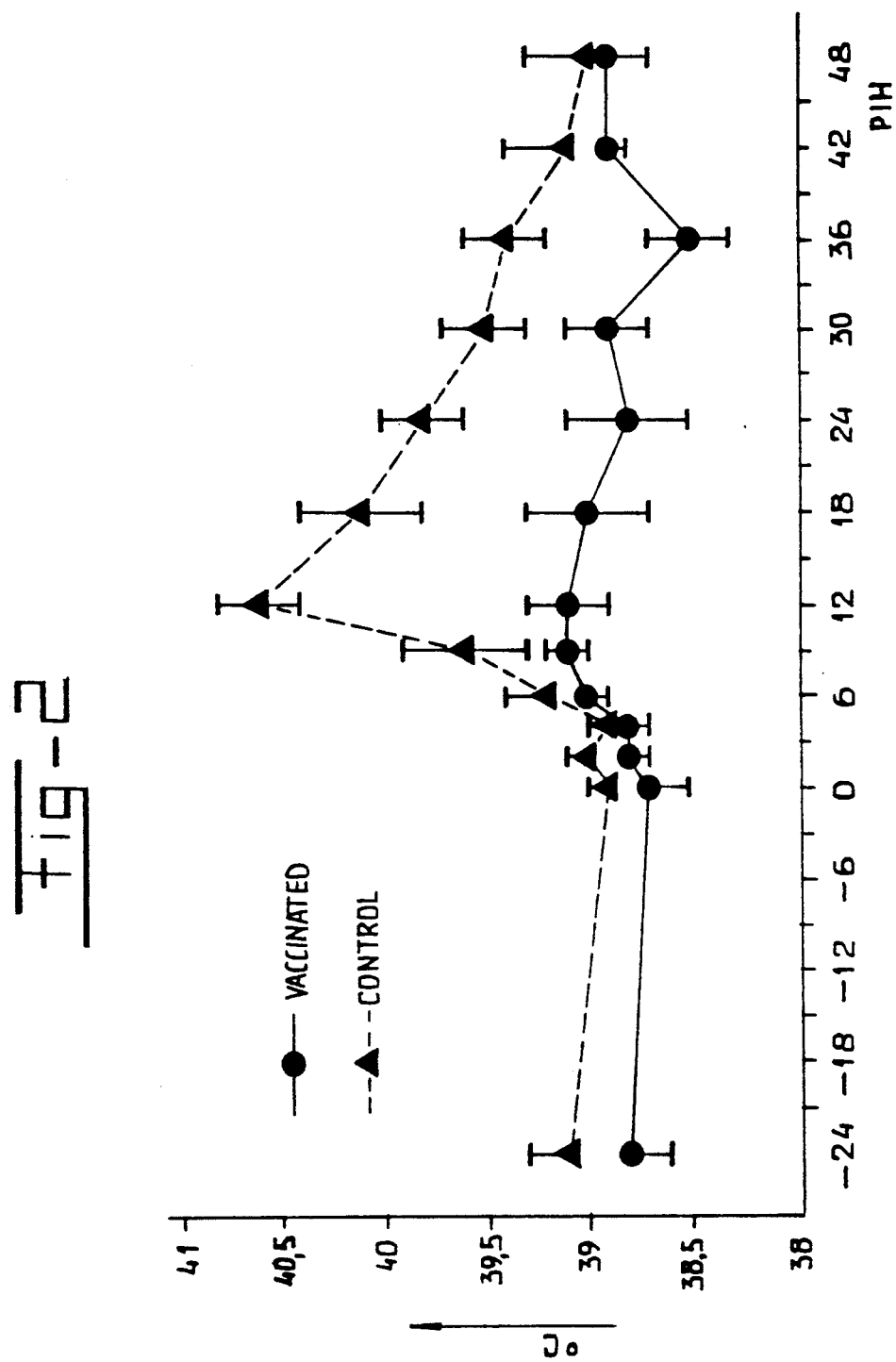
FIG. 2 is a graphic representation of the rectal temperatures ($\pm$SEM) of vaccinated and non-vaccinated pigs after endobronchial infection by $10^3$ CFU *H. pleuropneumoniae* strain 13261.

In contrast to the vaccinated pigs, which did not develop fever, the non-vaccinated pigs reached a fever peak at PIH 12 (see FIG. 2).

Figure 3:
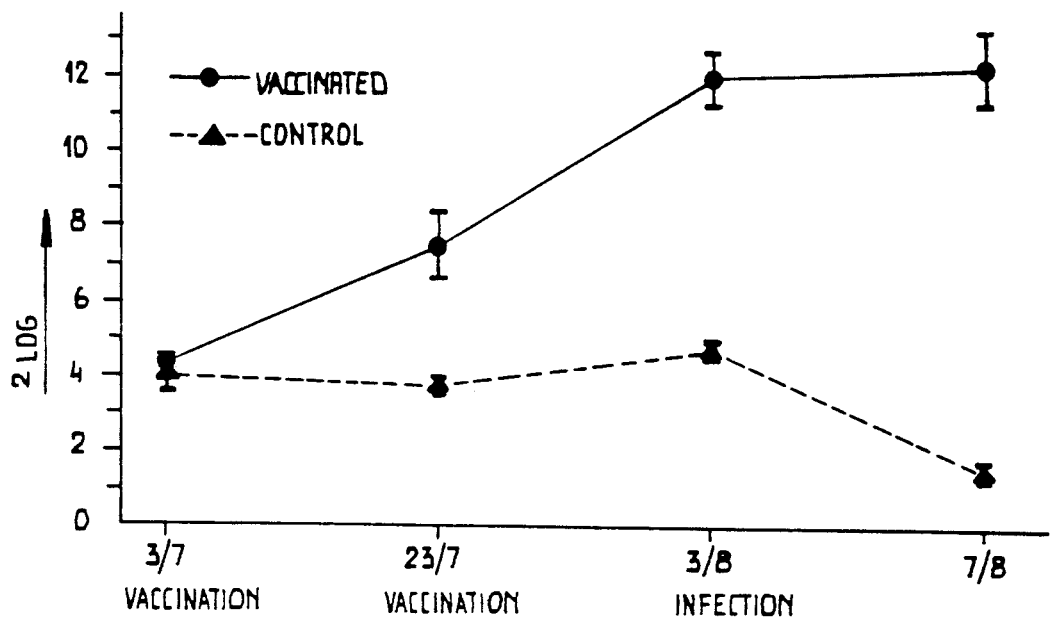
FIG. 3 is a graphic representation of the neutralizing antibodies against hemolysin of the *H. pleuropneumoniae* strain 13261 in vaccinated and non-vaccinated pigs.
Figure 4:
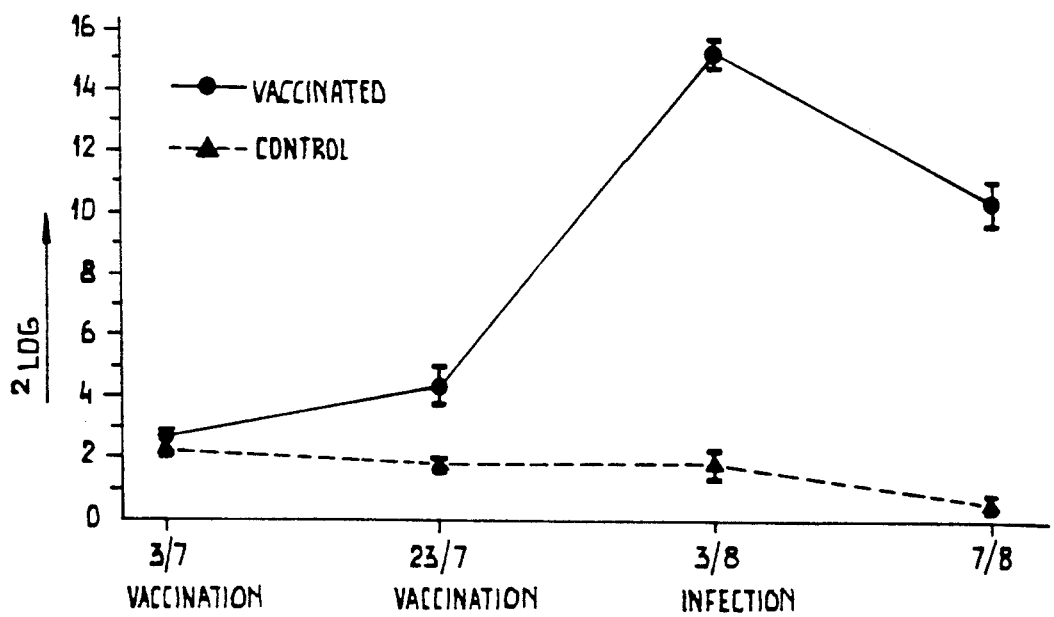
FIG. 4 is a graphic representation of the quantity of neutralizing antibodies against the cytotoxin of the *H. pleuropneumoniae* strain 13261 in vaccinated and non-vaccinated pigs.

Vaccinated pigs developed neutralising antibodies against hemolysin and cytotoxin of the $H.$ $pleuropneumoniae$ strain 13261 (see FIGS. 3 and 4).

At necropsy, all non-vaccinated pigs showed acute fibrinous hemorrhagic necrotic pleuropneumonia of the right diaphragmatic lobe of the lung which weighed approximately 75 g. None of the vaccinated pigs developed pneumonia except for one pig which developed local catarrhal pneumonia with foci of hemorrhages at the inoculation site. No induration or other abnormalities in the cervical muscles at the vaccination sited were observed.

It follows from the above that the pigs vaccinated with cytotoxin and hemolysin were protected against infection with $10^3$ CFU $H.pleuropneumoniae$ strain 13261. In contrast thereto, immunisation of pigs with whole-cell vaccines or with vaccines having capsular extracts of $H.pleuropneumoniae$ does not provide complete protection against a homologous infection (Rosendal, S., et al, 1986, Protective efficacy of capsule extracts of $Haemophilus$ $pleuropneumoniae$ in pigs. Vet. Microbiol., 12, pages 229-240).

In summary, it may be concluded that the efficacy of the $H.pleuropneumoniae$ vaccines according to the invention is based on the capability thereof to generate neutralising antibodies against $H.pleuropneumoniae$ toxins and not against their serotype-specific antigen properties.

We claim:

1. Vaccine suitable for prophylaxis and control of $Haemophilus$ $pleuropneumoniae$ in pigs, consisting essentially of a content of a mixture of hemolytic and cytotoxic proteinaceous materials, effective for producing protection against $Haemophilus$ $pleuropneumoniae$ in pigs, in the cell-free supernatants derived from the culture medium of:

both at least one $H.$ $pleuropneumoniae$ strain selected from the group consisting of serotypes 1, 5, 6, 9 and 11; and at least one $H.$ $pleuropneumoniae$ strain selected from the group consisting of serotypes 2, 3, 4 and 8.

2. Vaccine according to claim 1 including an effective content of a mixture of said proteinaceous materials obtained by sterile filtration of the culture medium of strains of at least two of said $H.$ $pleuropneumoniae$ serotypes.

* * * * *